US000001223H

United States Statutory Invention Registration [19]

[11] Reg. Number: H1223

Archibald et al. [43] Published: Aug. 3, 1993

[54] METHOD OF MAKING FLUORODINITROETHANOL (FDNE)

[75] Inventors: Thomas G. Archibald, Los Angeles; Nghi Van Nguyen, Monrovia; Kurt Baum, Pasadena, all of Calif.

[73] Assignee: The United States of America as represented by the Secretary of the Navy, Washington, D.C.

[21] Appl. No.: 702,215

[22] Filed: May 17, 1991

[51] Int. Cl.[5] ..... C07C 31/34; C07C 205/00

[52] U.S. Cl. ..... 568/947; 568/842; 568/924; 568/945; 568/948

[56] References Cited

PUBLICATIONS

Fluoronitroaliphatics-Fluorodinitromethyl Compounds *J. Org. Chem.* 33, No. 8, Aug. 1968, Kamlet, et al.

Aqueous Florination of Nitronate Salts *J. Org. Chem.* 33, No. 8, Aug. 1968, Grakauskas, et al.

*Primary Examiner*—Robert L. Stoll
*Assistant Examiner*—Shean C. Wu
*Attorney, Agent, or Firm*—James Busch; Alfons Kwitnieski; Thomas McDonald

[57] ABSTRACT

A method of producing FDNE using readily available fluoroolefins as a fluorine source.

5 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD OF MAKING FLUORODINITROETHANOL (FDNE)

BACKGROUND OF THE INVENTION

1. Field of Invention

This invention relates to a low cost method of making fluorodinitroethanol (FDNE) which is used as a plasticizer and binder in propellants and explosives.

2. Description of Prior Art

Two methods have been used previously for manufacturing fluorodinitroethanol and both have significant difficulties. One was based on the fluorination of nitroform and the other on the fluorination of 2,2-dinitropropanediol (A-diol). Nitroform was available at low cost from Sweden until the supply was curtailed by a plant explosion in the 1970's. Environmental and safety problems still inhibit resumption of the large-scale production of nitroform. In the alternate process, A-diol was deformylated with base and the salt fluorinated. This aqueous fluorination process was complicated by the formation of large amounts of insoluble sodium fluoride, the expense of the A-diol and difficulty in purifying the product. Both of these processes require elemental fluorine, with attendant high plant capital costs.

SUMMARY OF THE INVENTION

In the new process, readily available fluoroolefins are used as the fluorine source for FDNE. Nitration of 1,2-dichlorodifluoroethylene gives chlorofluoronitroacetic acid, and reaction of the latter with red fuming nitric acid gives chlorofluoronitronitrosomethane. Oxidation of chlorofluoronitronitrosomethane gives chlorofluorodinitromethane (CFDNM), and CFDNM is reduced in the presence of formaldehyde to give FDNE. These reactions are summarized below and the preliminary yields are given in Table I.

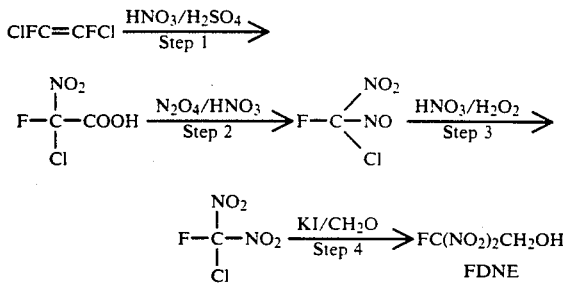

TABLE I

YIELDS OF REACTIONS LEADING TO FDNE

| STEP | STARTING MATERIAL | PRODUCT | YIELD |
|---|---|---|---|
| 1. | $ClFC{=}CFCl$ | $ClFCNO_2COOH$ | 77% |
| 2. | $ClFCNO_2COOH$ | $ClFCNO_2NO$ | 52% |
| 3. | $ClFCNO_2NO$ | $ClFC(NO_2)_2$ (CFDNM) | 62% |
| 4. | $ClFC(NO_2)_2$ | $FC(NO_2)CH_2OH$ (FDNE) | 71% |

DETAILED DESCRIPTION OF THE INVENTION 1,2-dichlorodifluoroethylene can be purchased commercially or can be prepared in 80% yield from commercially available 1,2-difluorotetrachloroethane by zinc mediated reduction, as taught by E. G. Locke, et al., *J. Am. Chem. Society* 1934, 56, 1726. The olefin from these sources was found to be an equal mixture of cis and trans isomers of 1,2-difluorotetrachloroethane, contaiminated by 10% of 1,1-difluorodichloroethylene. The source of the unsymmetrical isomer was found to be a 10% impurity of 1,1-difluorotetrachloroethane in the 1,2-difluorotetrachloroethane used as the starting material.

The results of the nitration reaction of the 1,2-dichlorodifluoroethylene with various solutions is shown in Table II below. A first solution of 99% nitric acid and 95% sulfuric acid yielded 34% chlorofluoronitroacetic acid.

The yield of chlorofluoronitroacetic acid in the nitration reaction was increased to 44% by replacing sulfuric acid with oleum. When a mixture of oleum, nitric acid and trifluoracetic acid was reacted with 1,2-dichlorodifluoroethylene, chlorofluoronitroacetic acid was obtained in 63% yield along with 14% of the 1,2-addition product, 1,2-dichloro-1,2-difluoro-2-nitroethyl trifluoroacetate, bringing the total yield of the nitration reaction to 77%. Apparently the 1,2-addition product was formed first and then was hydrolyzed in situ, to give the acetic acid derivative. The lower boiling point and diminished water sensitivity of the 1,2-addition product makes it a potentially attractive alternative to chlorofluoronitroacetic acid in subsequent nitration reactions.

TABLE II

CHLOROFLUORONITROACETIC ACID

| Solvent | Yield |
|---|---|
| 1. 95% $H_2SO_4$ 100% $HNO_3$ | 34% |
| 2. 30% Oleum 100% $HNO_3$ | 44% |
| 3. 30% Oleum, $CF_3COOH$ 100% $HNO_3$ | 77% |
| 4. 95% $H_2SO_4$, $CF_3COOH$ 100% $HNO_3$, $CH_2Cl_2$ | 50% |
| 5. $(CF_3CO)_2O$, $CH_2Cl_2$, 100% $HNO_3$ | 60% |

The chlorofluoronitritroacetic is next reacted with fuming nitric acid. When the reaction takes place at 80° C. in 90% nitric acid containing 20% $N_2O_4$, chlorofluornitronitrosomethane is isolated in 51% yield as an intensely blue liquid by distillation. This intermediate is stable for several days at ambient temperature, but is generally used directly in the next step without further isolation or purification.

Oxidation of chlorofluoronitronitrosomethane with 30% hydrogen peroxide in nitric acid at ambient temperature gave chlorofluorodinitromethane in 62% isolated yield. The reaction was 90% complete after 15 minutes as shown in Table III.

TABLE III

OXIDATION OF CHLOROFLUORONITRONITROSOMETHANE TO CFDNM

| TIME, MIN | $ClFC(NO_2)NO$ % | $ClFC(NO_2)_2$ % |
|---|---|---|
| 0 | 100 | 0 |
| 15 | 10.8 | 56.7 |
| 30 | 8.2 | 61.7 |
| 45 | 5.1 | 60. |

Chlorofluorodinitromethane can also be prepared by the direct aqueous fluorination of potassium chlorodinitromethane or by the reaction of chlorofluoronitroacetic acid with xenon difluoride.

FDNE has been prepared by reduction of fluorotrinitromethane with sodium hydroxide and hydrogen peroxide in the presence of formaldehyde. Attempted reduction of CFDNM under these conditions resulted in substantial hydrolysis to fluoride ion and the formation of small amounts of chlorofluoronitroethanol. Only trace amounts of FDNE were produced in aqueous or aqueous alcohol solvents, However, yields of FDNE as high as 71% were realized when KI was used as the reducing agent. Results using a 30% aqueous ethanolic solution of CFDNM (1 eq), KI (2.3 eq) and 30% formaldehyde solution (1.3 eq) at 70° C. are summarized in the Table IV. Formation of both FDNE and chlorofluoronitroethanol (CFNE) was observed with the maximum amount of FDNE observed at 1 h reaction time.

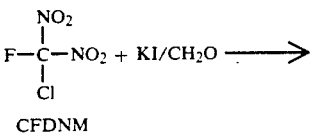

$FC(NO_2)_2CH_2OH$ + $ClFCNO_2CH_2OH$

FDNE 71% CFNE 29%

TABLE IV

REACTION OF CHLOROFLUORO-DINITROMETHANE (CFDNM) WITH $KI/CH_2O$

| Time at 70° C. min | CFDNM % | FDNE % | CFNE % | F % |
|---|---|---|---|---|
| 0 | 100 | — | — | — |
| 30 | 9.0 | 56.5 | 18.8 | 1.8 |
| 60 | 4.7 | 66.6 | 23.8 | 2.8 |
| 90 | 3.6 | 63.1 | 24.8 | 4.9 |
| 120 | 3.0 | 60.2 | 25.7 | 4.9 |

The effect of reaction variables on the yield of the reductive dehalogenation of CFDNM are summarized in Table V, where $^{19}F$ NMR is atomic weight 19 floride nuclear magnetic resonance. The reaction with KI was found to be slow at room temperature (RT), with less than 10% of the CFDNM reduced after 3 hours. Reactions conducted at 40° to 75° C. for short periods and then for several days as room temperature gave the best results. When the reaction temperature exceeded 75° C., no FDNE was formed and complete hydrolysis to fluoride ion occurred.

TABLE V

REDUCTIVE DEHALOGENATIONS OF CFDNM IN THE PRESENCE OF FORMALDEHYDE

| Protocols | Products (Yields from $^{19}F$ NMR integration) CFDNM | FDNE | CFME | F |
|---|---|---|---|---|
| $H_2O_2/NaOH/CH_2O$ in water 0° C., 1 h | trace | trace | 5% | 95% |
| $H_2O_2/NaOH/CH_2O$ in aq. MeOH 0° C. for 1 h then RT for 1 h | 5% | none | 2% | 95% |
| $H_2O_2/NaOH/CH_2O$ in aq. EtOH 0° C. for 1 h then RT for 1 h | 40% | trace | trace | 60% |
| $KI/CH_2O$ in aq. EtOH | | | | |
| 3 h at RT then | 90% | 5% | 5% | none |
| 2 days at RT | 8% | 50% | 34% | 5% |
| $KI/CH_2O$ in aq. EtOH | | | | |
| 2 h at 40° C. then | 33% | 44% | 23% | none |

TABLE V-continued

REDUCTIVE DEHALOGENATIONS OF CFDNM IN THE PRESENCE OF FORMALDEHYDE

| Protocols | Products (Yields from $^{19}F$ NMR integration) CFDNM | FDNE | CFME | F |
|---|---|---|---|---|
| 2 days at RT | none | 71% | 29% | trace |
| $KI/CH_2O$ in aq. EtOH | | | | |
| ½ h at 75° C. then | 15% | 58% | 24% | 3% |
| 2 days at RT | none | 67% | 30% | 3% |
| KI in aq. EtOH ½ h at 75° C. | none | none | trace | 99% |

Small amounts of chlorofluoronitroethanol (CFNE) were observed as a byproduct in most of the KI reductions. The boiling point of CFNE (40° C./0.4 mm) is closed to that of FDNE (41° C./0.1 mm) and these materials could not be separated readily by distillation. Pure chlorofluoronitroethanol was prepared for use as a reference standard by chlorination of 2-fluoro-2-nitro-1,3-propanediol in 45% yield. CFNE was also prepared in small yield by decarboxylation of chlorofluoronitroacetic acid in aqueous formaldehyde.

Reactions of CFDNM with various "soft" nucleophiles and reducing agents are summarized in Table VI below. The best results were obtained with sodium sulfide and sodium thiosulfate. However, sodium sulfide also reacted with formaldehyde to give insoluble trithiane. At room temperature, even after 16 h, these reactions were not complete. The reaction mixture containing sodium thiosulfate gave two phases after it was heated at 70° C. for 10 h. The aqueous phase showed only FDNE and the organic phase showed several unidentified products in addition to FDNE.

TABLE VI

REDUCTION OF CFDNM

| | Temp | FDNE | CFNE | F | Comments |
|---|---|---|---|---|---|
| KBr | RT | — | — | | No reaction |
| | 70° C. | — | — | | No reaction |
| $CH_3COOK$ | RT | — | — | | No reaction |
| | 70° C. | — | — | | No reaction |
| $NaNO_2$ | RT | — | — | | No reaction |
| | 70° C. | — | — | | No reaction |
| $Na_2SO_3$ | RT | — | — | | No reaction |
| | 70° C. | — | — | | No reaction |
| $K_3Fe(CN)_6$ | RT | — | — | | No reaction |
| | 70° C. | — | — | | No reaction |
| KOCN | RT | — | — | | No reaction |
| | 70° C. | 2% | 5% | 16% | Unreacted CFDNM |
| KCN | RT | 22% | 18% | 17% | Unreacted CFDNM |
| | 70° C. | 7% | 50% | 40% | |
| $Na_2S_2O_3$ | RT | 60% | trace | trace | Unreacted CFDNM |
| KSCN | RT | — | — | | No reaction |
| | 70° C. | 35% | trace | | Unreacted CFDNM Solid in mixture |
| $Na_2S$ | RT | 30% | trace | 40% | Unreacted CFDNM |
| | 70° C. | 50% | 7% | 40% | Water insoluble Solid in mixture |

Experimental

IR spectra were recorded in $CH_2Cl_2$ on a Perkin-Elmer 700 spectrometer. $^1H$, $^{13}C$ and $^{19}F$ NMR spectra were recorded in $CDCl_3$ on a Brucker AC200 spectrometer and are reported in ppm relative to TMS and $FCCl_3$. Warning: Fluorodinitroethanol is a powerful skin irritant.

Chlorofluoronitroacetic Acid, Sulfuric Acid Procedure. A solution of 100% $HNO_3$ (30 mL) in conc. $H_2SO_4$ (35 mL) was added over 30 min to neat 1,2-dichlorodifluoroethylene (48 g, 0.35 mol) at 10°-15° C.; an exothermic reaction was observed. The mixture was stirred for 10 min at 10° C. The organic layer was separated, and distilled to give 14 g (34%) of chlorofluoronitroacetic acid, bp 45°-65° C. (0.5 mm) (Lit[2]bp 90° C./8 mm): $^{19}F$ NMR ($CDCl_3$) δ −89.71; $^{13}C$ NMR δ113.69 (d, J=303 Hz), 161.21 (d, J=29 Hz).

Chlorofluoronitroacetic Acid, Oleum Procedure. A solution of 100% nitric acid (9 mL) in 30% oleum (11 mL) was added over 25 min to 1,2-dichlorodifluoroethylene (13.3 g, 0.1 mol) at 14°-17° C. The mixture was stirred for 30 min at 10°-14° C. The organic layer was separated, and distilled to give 6.84 g (44%) of chlorofluoronitroacetic acid, bp 80°-85° C. (8 mm), identical to the material prepared above.

Chlorofluoronitroacetic Acid, Oleum-Trifluoroacetic Acid Procedure. A solution of 100% nitric acid (5 mL) and trifluoroacetic acid (4.2 mL, 54 mmol) in 30% oleum (6 mL) was added over 25 min to 1,2-dichlorodifluoroethylene (7.5 g, 56 mmol) at 10°-15° C. The mixture was stirred for 60 min at 10°-14° C. The organic layer was separated, and fractionally distilled to give 2.1 g (14.5%) of 1,2-dichloro-1,2-difluoro-1-nitroethyl trifluoroacetate, as a 50:50 mixture of diasterimers, bp 48°-50° C. (0.5 mm): $^{19}F$ NMR ($CDCl_3$) δ −76.27 (s, 6 F), −77.50 (s,1 F), −78.49 (s, 1F), −94.37 (s, 1 F), −95.30 (s, 1 F). The second fraction contained 4.0 g of chlorofluoronitroacetic acid, bp 55°-65° C. (0.5 mm), identical to the authentic material prepared above. The oleum layer was heated to 80° C. under vacuum (0.5 mm) to give an additional 1.61 g (63% combined yield) of chlorofluoronitroacetic acid.

Chlorofluoronitronitrosomethane. Red fuming $HNO_3$ (7 mL) was added to a mixture of chlorofluoronitroacetic acid (2.4 g 15.3 mmol) and water (2 mL). The mixture was heated to 100° C. and the distillate boiling at 45°-92° C. was collected until the reaction mixture ceased to be blue in color. The blue distillate contained a mixture of $N_2O_4$ and 1.1 g (51%) of chlorofluoronitronitrosomethane (assayed by $^{19}F$ NMR using trifluorotoluene as the internal standard.) $^{19}F$ NMR ($CDCl_3$) −85.8 (t, J=10 Hz) (Lit[7] −85.6).

Chlorofluorodinitromethane from chlorofluoronitronitrosomethane. A solution of chlorofluoronitronitrosomethane (3.8 mg, 0.027 mmol) in 0.5 mL of $CDCl_3$ in an NMR tube was cooled to 5° C. and 0.2 mL of 100% $HNO_3$ and 0.1 mL of 30% $H_2O_2$ solution were added. The temperature was kept at 5° C. until the exothermic reaction subsided. The solution was then shaken at room temperature for 0.5 h until the blue color disappeared. The residue contained 2.5 mg (62% yield) of chlorofluorodinitromethane by $^{19}F$ NMR analysis (trifluorotoluene internal standard). This material was identical to authentic chlorofluorodi-nitromethane prepared above.

Fluorodinitroethanol from chlorofluorodinitromethane. A solution of chlorofluorodinitromethane (0.95 g, 6.0 mmol), KI (2.5 g, 15 mol), and 37% aqueous formaldehyde (0.6 ML, 7 mmol) in 30% aqueous ethanol (10 mL) was heated at 70° C. for 1 h. The solution was cooled and was found to contain 0.62 g (67%) of fluorodinitroethanol and 0.19 g (23%) of chlorofluoronitroethanol by $^{19}F$ NMR assay (trifluoroethanol internal standard).

Chlorofluoronitroethanol. A solution of 2-fluoro-2-nitro-1,3-propanediol (3.0 g, 21.6 mol) in of 12.5% bleach (NaClO, 100 mL) was stirred at ambient temperature for 3 h and then extracted with methylene chloride (2×100 mL). The combined organic solutions were dried ($MgSO_4$) and filtered through a pad of silica gel, and evaporated to give a yellow oil. The residual oil was distilled to give 1.3 g (42%) of chlorofluoronitroethanol, bp 39°-40° C. (0.4 mm): $^1H$ NMR ($CDCl_3$) δ3.58 (b, 1H), 4.16-4.49 (m, 2H); $^{13}C$ NMR ($CDCl_3$) δ62.69 (d, J=23.7 Hz), 119.97 (d, J=293.2 Hz); $^{19}F$ NMR ($CDCl_3$) δ 98.19 (dd, J=6.8, 22 Hz). Anal. Calcd for $C_2H_3ClFNO_3$: C,16.75; H, 2.11; N,9.76. Found: C, 16.72; H, 2.37; N, 9.68.

We claim:

1. A method of producing fluorodinitroethanol (FDNE) comprising the steps of:

A. Reacting 1,2-dichorodifluoroethylene with a mixture containing a nitrate to obtain chlorofluoronitroacetic acid;

B. reacting said chlorofluoronitroacetic acid with nitric acid to obtain chlorofluoronitronitrosomethane;

C. oxidizing the said chlorofluoronitronitrosomethane to obtain chlorofluorodinitromethane (CFDNM); and D. reducing said CFDNM in the presence of formaldehyde to produce FDNE.

2. The process of claim 1 in which the initial reaction of 1,2-dichlorofluoroethylene is with a mixture of oleum, nitric acid and trifluoroacetic acid.

3. The process of claim 2 in which said chlorofluoronitronitrosomethane is oxidized with about 30% hydrogen peroxide in nitric acid.

4. The process of claim 3 in which said CFDNM is reduced with KI as the reducing agent.

5. The process of claim 3 in which $KI/CH_2O$ in aqueous EtOH is used as the reducing agent for 2 hours at 40° C. and then 2 days at room temperature.

* * * * *